United States Patent
Picker et al.

(10) Patent No.: US 12,257,262 B2
(45) Date of Patent: *Mar. 25, 2025

(54) METHOD OF RECONSTITUTING LIPOSOMAL ANNAMYCIN

(71) Applicants: Board of Regents, The University of Texas System, Austin, TX (US); Moleculin Biotech, Inc., Houston, TX (US)

(72) Inventors: Donald Picker, Albany, NY (US); Waldemar Priebe, Houston, TX (US)

(73) Assignees: Board of Regents, The University of Texas System, Austin, TX (US); Moleculin Biotech, Inc., Houston, TX (US)

(*) Notice: Subject to any disclaimer, the term of this patent is extended or adjusted under 35 U.S.C. 154(b) by 472 days.

This patent is subject to a terminal disclaimer.

(21) Appl. No.: 17/554,553

(22) Filed: Dec. 17, 2021

(65) Prior Publication Data

US 2022/0105116 A1    Apr. 7, 2022

Related U.S. Application Data

(63) Continuation of application No. PCT/US2020/039621, filed on Jun. 25, 2020.

(60) Provisional application No. 62/868,190, filed on Jun. 28, 2019.

(51) Int. Cl.
*A61K 31/704* (2006.01)
*A61K 9/00* (2006.01)
*A61K 9/127* (2006.01)

(52) U.S. Cl.
CPC .......... *A61K 31/704* (2013.01); *A61K 9/0019* (2013.01); *A61K 9/127* (2013.01)

(58) Field of Classification Search
CPC .... A61K 31/704; A61K 9/0019; A61K 9/127; A61K 9/1277; A61K 47/26; A61P 35/02
See application file for complete search history.

(56) References Cited

U.S. PATENT DOCUMENTS

| 4,863,739 | A | 9/1989 | Perez-Soler |
| 5,902,604 | A | 5/1999 | Zou |
| 7,238,366 | B1 * | 7/2007 | Zou ...................... A61K 9/1277 264/4.1 |
| 11,980,634 | B2 | 5/2024 | Picker |

(Continued)

FOREIGN PATENT DOCUMENTS

| WO | 1988009168 | 12/1988 |
| WO | 1996039121 | 12/1996 |

(Continued)

OTHER PUBLICATIONS

Zou et al, "Organ distribution and tumor uptake of annamycin, a new anthracycline derivative with high affinity for lipid membranes, entrapped in multilamellar vesicles", Cancer Chemother Pharmacol, 1993, 32, pp. 190-196 (Year: 1993).*

(Continued)

*Primary Examiner* — Benjamin J Packard
*Assistant Examiner* — Joshua A Atkinson
(74) *Attorney, Agent, or Firm* — Global Patent Group Inc.; Cynthia Hathaway; Erik M. Larsen

(57) ABSTRACT

Methods of reconstituting lyophilized Annamycin and methods of treating patients are described.

16 Claims, 4 Drawing Sheets

(56) References Cited

U.S. PATENT DOCUMENTS

| | | | |
|---|---|---|---|
| 2004/0057989 A1* | 3/2004 | Andreeff | A61K 31/20 |
| | | | 435/7.23 |
| 2005/0238707 A1 | 10/2005 | Andreeff | |
| 2013/0195963 A1 | 8/2013 | Serda | |
| 2014/0308339 A1 | 10/2014 | Ryan | |
| 2016/0175438 A1* | 6/2016 | Alavattam | A61K 31/337 |
| | | | 424/133.1 |
| 2017/0209574 A1 | 7/2017 | Cao | |
| 2017/0281624 A1 | 10/2017 | Peters | |
| 2022/0105115 A1 | 4/2022 | Picker | |

FOREIGN PATENT DOCUMENTS

| | | |
|---|---|---|
| WO | 2001032145 | 5/2001 |
| WO | 2018048752 | 3/2018 |
| WO | 2020101790 | 5/2020 |
| WO | 2020264160 | 12/2020 |
| WO | 2020264161 | 12/2020 |
| WO | 2021102404 | 5/2021 |

OTHER PUBLICATIONS

Wetzler et al, "Phase I/II Trial of Nanomolecular Liposomal Annamycin in Adult Patients With Relapsed/Refractory Acute Lymphoblastic Leukemia", Clinal Lympohoma, Myeloma & Luekemia, 2013, vol. 13, No. 4, pp. 430-434 (Year: 2013).*
Bulbake, U. et al., "Liposomal Formulations in Clinical Use: An Updated Review", Pharmaceutics, 9(2):12, (2017).
Cullis, P. et al., "Generating and loading of liposomal systems for drug-delivery applications", Adv Drug Deliv Rev., 3:267-82, (1989).
Hanawa, T. et al., Medicine, vol. 74(1):57-62, (2014).
International Application No. PCT/US2020/039620; International Preliminary Report on Patentability, date of issuance Jan. 6, 2022; 7 pages.
International Application No. PCT/US2020/039620; International Search Report and Written Opinion of the International Searching Authority, date of mailing Oct. 1, 2020; 10 pages.
International Application No. PCT/US2020/039621; International Preliminary Report on Patentability, date of issuance Jan. 6, 2022; 6 pages.
International Application No. PCT/US2020/039621; International Search Report and Written Opinion of the International Searching Authority, date of mailing Oct. 1, 2020; 8 pages.
International Application No. PCT/US2020/061775; International Preliminary Report on Patentability, date of issuance Jun. 9, 2022; 6 pages.
International Application No. PCT/US2020/061775; International Search Report and Written Opinion of the International Searching Authority, date of mailing Feb. 11, 2021; 8 pages.
Lauraeus, S. et al., "Aggregation of dimyristoylphosphatidylglycerol liposomes by human plasma low density lipoprotein", 1373(1):147-62, (1998).
Moleculin Biotech, Inc., "Moleculin Announces Significant Discovery in Lung Cancer Models", PR Newswire, retrieved at https://www.prnewswire.com/news-releases/moleculin-announces-significant-discovery-in-lung-cancer-models-300833462.html, 3 pages, (dated Apr. 2019).
Moleculin, "Moleculin Increases Annamycin Production Due to Positive Clinical Trial Activity and Expanded Potential Indications", created Oct. 22, 2019.
Pérez-Herrero, E. et al., "Advanced targeted therapies in cancer: Drug nanocarriers, the future of chemotherapy", Eur J Pharm Biopharm., 93:52-79, (2015).
Perez-Soler, R. et al., "Annamycin circumvents resistance mediated by the multidrug resistance-associated protein (MRP) in breast MCF-7 and small-cell lung UMCC-1 cancer cell lines selected for resistance to etoposide", Int J Cancer, 71(1):35-41, (1997).
Perez-Soler, R., "Treatment of Metastatic Breast Carcinoma Refractory to Doxorubicin With Liposomal-Annamycin", US Army Med Res Mat Command Annual Report, pp. 5-16, 24-34, (1997).
U.S. Appl. No. 17/554,550; Applicant-Initiated Interview Summary, date of interview Nov. 14, 2024; 2 pages.
U.S. Appl. No. 17/554,550; Non-Final Office Action, dated Sep. 5, 2024; 13 pages.
Zou, Y. et al., "Antitumor Activity of Free and Liposome-entrapped Annamycin, a Lipophilic Anthracycline Antibiotic with Non-Cross-Resistance Properties", Cancer Res., 54(6):1479-84, (1994).
Zou, Y. et al., "Antitumor Activity of Free and Liposome-entrapped Annamycin, a Lipophilic Anthracycline Antibiotic with Non-Cross-Resistance Properties", Cancer Res., 54(6):1479-84, Abstract only, (1994).
Zou, Y. et al., "Lyophilized Preliposomal Formulation of the Non-Cross-Resistant Anthracycline Annamycin: Effect of Surfactant on Liposome Formation, Stability and Size", Cancer Chemother Pharmacol., 39(1-2):103-8, (1996).
Zou, Y. et al., "Organ distribution and tumor uptake of annamycin, a new anthracycline derivative with high affinity for lipid membranes, entrapped in multilamellar vesicles", Cancer Chemother Pharmacol., 32(3):190-6, Abstract only, (1993).
Zou, Y. et al., "Preclinical toxicity of liposome-incorporated annamycin: selective bone marrow toxicity with lack of cardiotoxicity", Clin Cancer Res., 1(11):1369-74, (1995).

* cited by examiner

METHOD OF RECONSTITUTING LIPOSOMAL ANNAMYCIN

This application is a bypass continuation of International Application No. PCT/US2020/039621, filed Jun. 25, 2020, which claims the benefit of priority of U.S. Provisional Application No. 62/868,190, filed Jun. 28, 2019, the disclosures of which are hereby incorporated by reference as if written herein in their entireties.

Annamycin is a cancer chemotherapeutic agent of the anthracene structural family. Because of its physical and pharmacological properties, compositions of Annamycin for dosage forms have been described in which the drug is formulated as a liposome (See U.S. Pat. No. 7,238,366). Clinical trials have been described for liposomal Annamycin in adult patients with relapsed refractory Acute lymphoblastic leukemia (M. Wetzler, et al., Clinical Lymphoma, Myeloma and Leukemia, 13 (4), 430-434 August 2013) and in the treatment of doxorubicin-resistant breast cancer (D. J. Booser et al., Cancer Chemother. Pharmacol. 50; 6-8, 2002).

In drug delivery systems, it is desirable to be able to produce a drug formulation that is of consistent purity and quality in order to ensure that the correct dosage is administered, thus providing the most efficacious treatment, while avoiding unwanted side effects caused by impurities. Furthermore, poorly maintained or improperly formulated drug material can decompose prior to administration, rendering it ineffective, resulting in waste of costly active pharmaceutical ingredients. Regulatory standards also necessitate that a consistent level of purity of drug and amount of drug be provided by following the procedures specified on the label.

Annamycin presents particularly difficult formulation challenges because of its inherent physical properties, and because of inherent instability of both the parent drug and of liposomal formulation under certain conditions. It would therefore be advantageous to find a consistent method for preparing a dosage form of liposomal Annamycin that assures purity and avoids decomposition.

SUMMARY

Provided is a method of reconstituting a preliposomal Annamycin lyophilizate to form a liposomal Annamycin suspension.

Also provide is a method of reconstituting Annamycin, such method comprising:
adding pre-warmed saline to one or more containers of preliposomal Annamycin lyophilizate, to form suspended liposomal Annamycin with a concentration of about 0.5-1.5 mg/mL;
maintaining said one or more containers at 24-45° C.;
diluting said suspended liposomal Annamycin, with pre-warmed saline to provide liposomal Annamycin at a concentration in saline of about 0.5-1.5 mg/mL; and
maintaining said one or more containers of suspended liposomal Annamycin and said diluted liposomal Annamycin at 24-45° C. during and after the dilution.

Also provided is a method of preparing an effective dose of a reconstituted liposomal formulation of Annamycin, such method comprising:
warming syringes and non-PVC IV bags, each containing saline (about) 0.9% aqueous injection USP sodium chloride at 37° C.±4° C. for at least about three hours, in an oven or bag warmer, wherein
the volume of saline in mL in a syringe is equal to the weight in mg of preliposomal lyophilizate Annamycin to be reconstituted, and
the volume of saline within said IV bag equivalent to the total amount of saline in all syringes, and
the volume of said IV bag is of sufficient capacity to contain the total volume of saline and liposomal Annamycin. for dilution of the total dose of liposomal Annamycin;
removing a sufficient number of vials containing preliposomal Annamycin lyophilizate to provide the desired total dose of Annamycin from the freezer and allowing the vials to stand at room temperature for 30 minutes to 2 hours;
vigorously shaking each vial of preliposomal lyophilizate Annamycin to break up any dry cake;
injecting air into each vial from air filled syringes until pressure in each vial is equalized;
adding a volume of 37° C.±4° C. saline from a syringe kept at 37° C.±4° C. in an oven to a vial containing a weight equivalent vial of preliposomal lyophilizate Annamycin such that the final Annamycin concentration is approximately 1 mg/mL, maintaining negative pressure throughout the addition of saline;
immediately shaking the vial back and forth vigorously by hand for 15 seconds, then placing the vial in a resealable polyethylene storage bag;
repeating the addition of saline, shaking the vial, and placing the vial in the storage bag until all vials required for the total dose of Annamycin are similarly prepared;
shaking, for a second time, all vials, 2-4 at a time for 1-2 minutes;
storing all vials of reconstituted liposomal Annamycin at 37° C.±4° C. until ready for dilution, for 30 minutes up to 1 hour;
removing vials of reconstituted liposomal Annamycin from storage at 37° C.±4° C. no more than two at a time, and after gently inverting each vial once, withdrawing a foam-free suspension from the vial while maintaining negative pressure throughout the withdrawal of the suspension;
introducing the withdrawn foam-free suspension of reconstituted liposomal Annamycin slowly into a pre-warmed non-PVC IV bag of saline, prepared as described above and repeating this process for the second vial;
repeating the steps of removing the vials, withdrawing the suspension, and introducing the suspension into the prewarmed IV bag until all vials of reconstituted liposomal Annamycin required for the total dose of Annamycin have been introduced into the non-PVC IV bag, providing an IV bag containing the final reconstituted liposomal Annamycin with a concentration of about 0.5 mg/mL; and
agitating the saline and reconstituted liposomal Annamycin in the IV bag by gently inverting the container several times, without generating foam.

Also provided is a method of treating cancer comprising administering to a patient in need thereof, an effective dose of diluted liposomal Annamycin prepared by
adding pre-warmed saline to one or more containers of preliposomal Annamycin lyophilizate, to form a liposomal Annamycin suspension with a concentration of about 0.5-1.5 mg/mL;
maintaining said one or more containers at 24-45° C.;
diluting said suspended liposomal Annamycin, with pre-warmed saline to provide liposomal Annamycin at a concentration in saline of about 0.3-0.7 mg/mL; and maintaining said one or more containers of suspended liposomal Annamycin and said diluted liposomal Annamycin at 24-45° C. during and after the dilution.

Also provided is a use of diluted reconstituted liposomal Annamycin prepared according to the above methods, in the manufacture of a medicament for the treatment of cancer.

Also provided is a diluted reconstituted liposomal Annamycin prepared according to the above methods, for use in the treatment of cancer.

DETAILED DESCRIPTION

Figure 1:
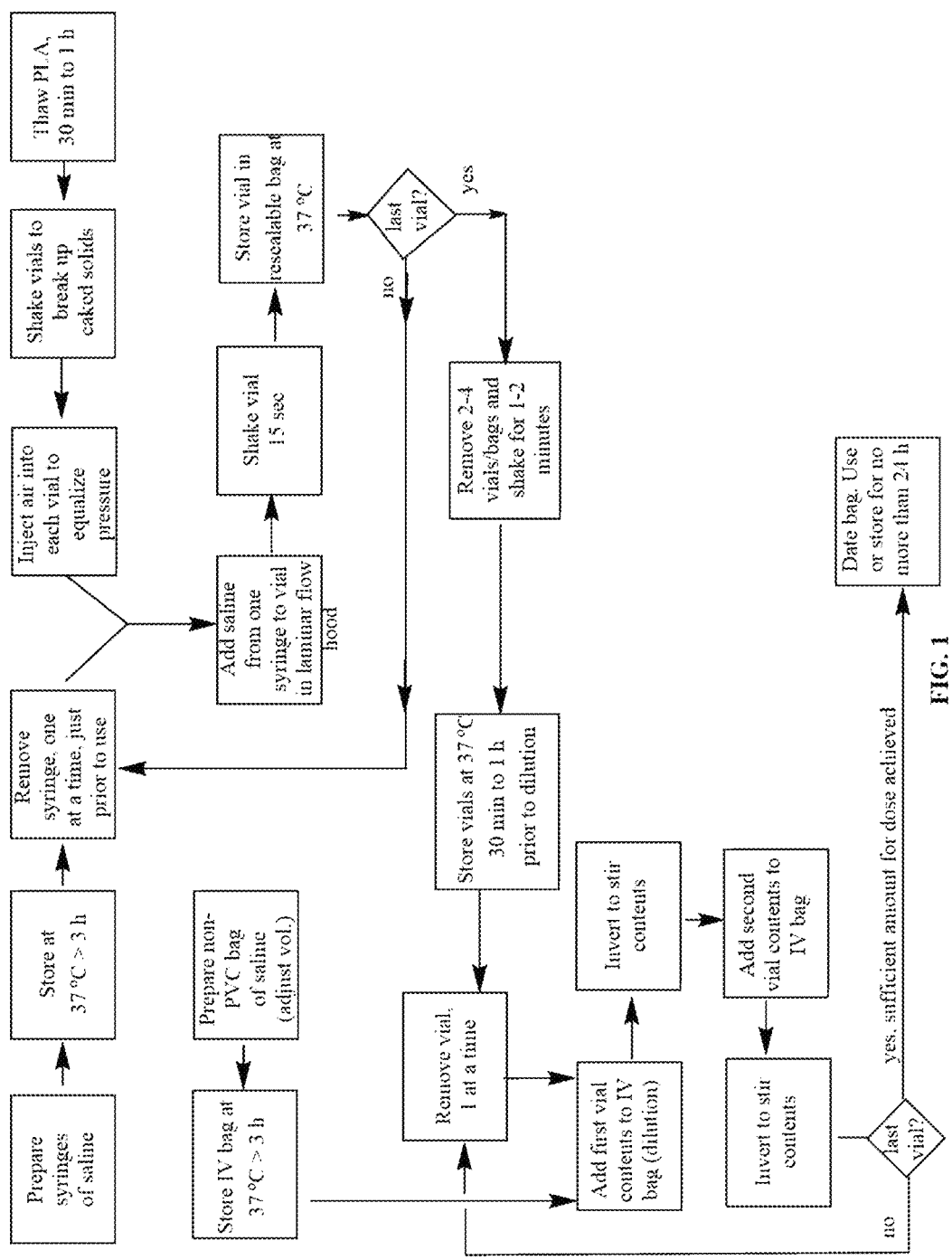
FIG. 1. A schematic representation, exemplifying the method for reconstituting liposomal Annamycin from preliposomal Annamycin lyophilizate.

Provided is a method of making a formulation of liposomal Annamycin with improved stability and high purity.
Definitions
Unless defined otherwise, all technical and scientific terms used herein have the same meaning as is commonly understood by one of skill in the art to which the invention(s) belong.

As used herein, the following terms have the meaning as defined below.

The term "Annamycin" shall mean the compound (7S, 9S)-7-(((2R,3R,4R,5R,6S)-4,5-dihydroxy-3-iodo-6-methyl-tetrahydro-2H-pyran-2-yl)oxy)-6,9,11-trihydroxy-9-(2-hydroxyacetyl)-7,8,9,10-tetrahydrotetracene-5,12-dione, having the following structure:

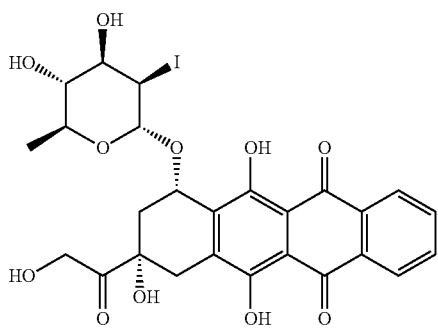 [SMILES: C[C@@H]1O[C@@H](O[C@H]2C[C@](O)(C(=O)CO)Cc3c(O)c4c(c(O)c32)C(=O)c2ccccc2C4=O)[C@H](I)[C@H](O)[C@H]1O]

The term "liposomes," "liposomal," and the like shall mean generally spherical structures comprising lipids, fatty acids, lipid bilayer type structures, unilamellar vesicles and amorphous lipid vesicles. Classically, liposomes are completely closed lipid bilayer membranes containing an entrapped aqueous volume. Liposomes include non-classical forms where the Annamycin may be inside the bilayer, part of the bilayer, and absorbed onto the bilayer. Liposomes may be unilamellar vesicles (possessing a single bilayer membrane) or multilamellar vesicles (onion-like structures characterized by multiple membrane bilayers, each separated from the next by an aqueous layer). The bilayer is composed of two lipid monolayers having a hydrophobic "tail" region and a hydrophilic "head" region. The structure of the membrane bilayer is such that the hydrophobic (nonpolar) "tails" of the lipid monolayers orient toward the center of the bilayer while the hydrophilic "head" orient towards the aqueous phase.

The term "preliposome-lyophilizate" and "preliposomal lyophilizate" shall mean a non-aqueous material that will form liposomes upon addition of aqueous solution. In some embodiments the non-aqueous material is dry (as in non-liquid, non-gel) material. Lyophilizate is used expansively to include the dry residue of sublimation of frozen liquids from non-volatile materials, the residue of roto evaporation and similar procedures, and dry compositions that, upon addition of an aqueous phase (with or without agitation) will result in liposomes. It is particularly to be understood that "preliposome-lyophilizate" is not in liposomal form after lyophilization.

The term "preliposomal Annamycin lyophilizate" is one preliposome-lyophilizate where the drug is Annamycin. In some embodiments, the lyophilizate is prepared according to the procedures set forth in U.S. Patent Publication 2005/0238707, which is incorporated herein by reference for all purposes.

The term "pre-warmed" means that the article or solution or suspension is warmed to a temperature of about 24-45° C., such as 30-45° C., for example, 37° C.±4° C., or 37° C.±2° C., 37° C.±1° C.

The term "high purity Annamycin preliposomal lyophilizate" shall mean purity of material which is no less than 95% Annamycin as analyzed by HPLC using a verified standard sample. In some embodiments, the Annamycin is at least 96% pure, or at least 97% pure, or at least 98% pure, or at least 99% pure.

In the foregoing sections, a number of abbreviations and acronyms were used, and the full description of these are provided as follows:
DMPC dimyristoyl phosphatidylcholine
DMPG 1,2-dimyristoyl-sn-glycero-3-phospho-(1'-rac- glycerol) (sodium salt)
DMSO dimethyl sulfoxide
IV intravenous
DEHP bis(2-ethylhexyl) phthalate
PLA preliposomal lyophilized Annamycin
PVC polyvinyl chloride
WFI water for injection; in compliance with USP Throughout this specification and in the claims that follow, unless the context requires otherwise, the word "comprise", or variations such as "comprises" or "comprising", should be understood to imply the inclusion of a stated integer or step or group of integers or steps but not the exclusion of any other integer or step or group of integers or steps. It is intended herein that by recitation of such specified ranges, the ranges recited also include all those specific integer amounts between the cited ranges. For example, the range of about 24-45° C., it is intended to also encompass 24, 30, 33, 34, 35, 36, 37, 38, 39, 40, and 45° C.

The entire disclosure of each United States patent and international patent application mentioned in this patent specification is fully incorporated by reference herein for all purposes.

Also provided is a method of making a liposomal Annamycin that has superior uniformity and stability. Provided is a novel method of making a liposomal Annamycin that has superior uniformity and stability. In particular, provided is a method of reconstituting Annamycin, such method comprising:

adding pre-warmed saline to one or more containers of preliposomal Annamycin lyophilizate, to form suspended liposomal Annamycin with a concentration of about 0.5-1.5 mg/mL;

maintaining said one or more containers at 24-45° C.;

diluting said suspended liposomal Annamycin, with pre-warmed saline to provide liposomal Annamycin at a concentration in saline of about 0.5-1.5 mg/mL; and maintaining said one or more containers of suspended liposomal Annamycin and said diluted liposomal Annamycin at 24-45° C. during and after the dilution.

In some embodiments, the liposomal Annamycin suspension has a concentration of 0.5-1.5 mg/mL In some embodiments, the liposomal Annamycin suspension has a concentration of 0.8-1.2 mg/mL. In some embodiments, the liposomal Annamycin suspension has a concentration of about 1 mg/mL.

In some embodiments, the total weight of the Annamycin in the diluted suspension added into a pre-warmed saline containing IV bag is equal to the effective dose required.

In some embodiments, the suspended liposomal Annamycin is diluted by adding it into a pre-warmed saline-containing IV bag. In some embodiments, the saline-containing IV bag is at a temperature of 30-45° C. In some embodiments, the saline-containing IV bag is at a temperature of 37° C.±4° C.

In some embodiments, the reconstituted liposomal Annamycin is formed at or above 24° C. In some embodiments, the reconstituted liposomal Annamycin is maintained at or above 24° C. prior to and during dilution, and prior to and during infusion. It was surprisingly found that liposomal Annamycin was unstable below 24° C.

In some embodiments, the reconstituted liposomal Annamycin is maintained at a temperature of 30-45° C. In some embodiments, the reconstituted liposomal Annamycin is maintained at a temperature of 30-42° C. In some embodiments, the reconstituted liposomal Annamycin is maintained at a temperature of 37° C.±4° C. In some embodiments, the suspension of liposomal Annamycin is maintained at or near 37° C. and the diluted liposomal Annamycin is maintained at or near 37° C.

In some embodiments, the diluted liposomal Annamycin has a concentration of about 0.5 mg/mL.

In some embodiments, a protective sleeve is used on the IV drip line to ensure that the diluted liposomal Annamycin is delivered at a temperature of at or above 37° C.±4° C. In some embodiments, the sleeve is heated. In some embodiments, the sleeve is insulated.

In some embodiments, the method of reconstituting Annamycin, comprises:

adding saline at 37° C.±4° C. to one or more containers of preliposomal Annamycin lyophilizate, to form suspended liposomal Annamycin with a concentration of about 1 mg/mL;

maintaining said one or more containers at 37° C.±4° C.;

diluting said suspended liposomal Annamycin, with saline at 37° C.±4° C. to provide liposomal Annamycin at a concentration in saline of about 0.5 mg/mL; and maintaining said one or more containers of suspended liposomal Annamycin and said diluted liposomal Annamycin at 37° C.±4° C. during and after the dilution.

In some embodiments, the diluted liposomal Annamycin is maintained at 37° C.±4° C. prior to and during administration.

In some embodiments, the container of the lyophilized Annamycin is a vial having at least 4 mL of headspace after the addition of the pre-warmed saline to allow sufficient mixing to form the liposomes. In some embodiments, the vial is a 50 mL size.

In some embodiments, the method of preparing an effective dose of a reconstituted liposomal formulation of Annamycin comprises:

warming syringes and non-PVC IV bags, each containing saline (about) 0.9% aqueous injection USP sodium chloride at 37° C.±4° C. for at least about three hours, in an oven or bag warmer, wherein the volume of saline in mL in a syringe is equal to the weight in mg of preliposomal lyophilizate Annamycin to be reconstituted, and the volume of saline within said IV bag equivalent to the total amount of saline in all syringes, and the volume of said IV bag is of sufficient capacity to contain the total volume of saline and liposomal Annamycin. for dilution of the total dose of liposomal Annamycin;

removing a sufficient number of vials containing preliposomal Annamycin lyophilizate to provide the desired total dose of Annamycin from the freezer and allowing the vials to stand at room temperature for 30 minutes to 2 hours;

vigorously shaking each vial of preliposomal lyophilizate Annamycin to break up any dry cake;

injecting air into each vial from air filled syringes until pressure in each vial is equalized;

adding a volume of 37° C.±4° C. saline from a syringe kept at 37° C.±4° C. in an oven to a vial containing a weight equivalent vial of preliposomal lyophilizate Annamycin such that the final Annamycin concentration is approximately 1 mg/mL, maintaining negative pressure throughout the addition of saline;

immediately shaking the vial back and forth vigorously by hand for 15 seconds, then placing the vial in a resealable polyethylene storage bag;

repeating the steps of adding saline, shaking the vial, and placing the vial in the storage bag, until all vials required for the total dose of Annamycin are similarly prepared;

shaking, for a second time, all vials, 2-4 at a time for 1-2 minutes;

storing all vials of reconstituted liposomal Annamycin at 37° C.±4° C. until ready for dilution, for 30 minutes up to 1 hour;

removing vials of reconstituted liposomal Annamycin from storage at 37° C.±4° C. no more than two at a time, and after gently inverting each vial once, withdrawing a foam-free suspension from the vial while maintaining negative pressure throughout the withdrawal of the suspension;

introducing the withdrawn foam-free suspension of reconstituted liposomal Annamycin slowly into a pre-warmed non-PVC IV bag of saline, prepared as described in above and repeating this process for the second vial;

repeating the steps of removing the vials, withdrawing the suspension, and introducing the suspension into the pre-warmed IV bag, until all vials of reconstituted liposomal Annamycin required for the total dose of Annamycin have been introduced into the non-PVC IV bag, providing an IV bag containing the final reconstituted liposomal Annamycin with a concentration of about 0.5 mg/mL; and agitating the saline and reconstituted liposomal Annamycin in the IV bag by gently inverting the container several times, without generating foam.

In some embodiments, the preliposomal Annamycin lyophilizate is comprised of Annamycin, one or more lipids, and one or more non-ionic surfactants. In some embodiments, the lipids comprise DMPC and DMPG, and the non-ionic surfactant comprises a polysorbate-type surfactant formed from the ethoxylation of sorbitan followed by the addition of a carboxylic acid. In some embodiments, the non-ionic surfactant comprises polyoxyethylene sorbitan monolaurate. In some embodiments, the preliposomal Annamycin lyophilizate comprises 1.8-2.2 wt % Annamycin; 3.0-3.4 wt. % Polysorbate 20; and 94.4-95.2 wt. % of lipids selected from DMPC and DMPG. In some embodiments, the DMPC is 65.3-67.3 wt. % and the DMPG is 27.1-29.9 wt. %.

Also provided is a method of treatment via infusion to patients in need thereof, of an effective dose of a reconstituted liposomal Annamycin, prepared from preliposomal Annamycin lyophilizate by the above described method wherein the temperature of the liposomal formulation was maintained at 37° C. ±4° C. throughout reconstitution and administration and used within 24 hours.

Also provided is the use of the above described reconstituted liposomal Annamycin for the treatment of cancer comprising administering to a patient in need thereof an effective dose of diluted liposomal Annamycin prepared as described above. In some embodiments, the cancer is selected from breast cancer, leukemia, acute myeloid leukemia, acute lymphoblastic leukemia, gastric cancer, Hodgkin and non-Hodgkin lymphoma, ovarian cancer, thyroid cancer, colon cancer, traditional cell bladder cancer, and Wilms tumor.

The reconstituted liposomal Annamycin prepared as described herein is useful for treatment of certain human cancer, such as breast cancer; leukemia, including acute myeloid leukemia (AML) and acute lymphoblastic leukemia; gastric cancer; Hodgkin and non-Hodgkin lymphoma; ovarian cancer; thyroid cancer; colon cancer; traditional cell bladder cancer; and Wilms tumor.

Dosages and Routes of Administration.

In general, the reconstituted liposomal formulation is used within 24 h of reconstitution for the treatment of patients with the conditions for which treatment would be beneficial. Administering the drug intravenously is achieved by standard means, and depending on dosage amount, is completed within 110 to 130 min.

Liposomal Annamycin is used in methods of treating cancer and in methods of inhibiting the growth of tumors in mammals, particularly in humans. Cancer that may be treated include leukemias and lymphomas. In particular, Annamycin may be used in the treatment of leukemias including acute myeloid leukemia (AML), chronic myeloid leukemia (CML), acute lymphocytic leukemia (ALL), and chronic lymphocytic leukemia (CLL). Liposomal Annamycin may be used in the treatment of lymphomas including Hodgkin and non-Hodgkin lymphoma. The methods involve administering to a mammal an effective amount of the drug composition.

The administering step can suitably be parenteral and by intravenous, intraarterial, intramuscular, intralymphatic, intraperitoneal, subcutaneous, intrapleural, intrathecal injection, or by topical application dosage. In some embodiments the Annamycin is administered intraveniously. In some embodiments, such administration is a repeated dose regimen until tumor regression or disappearance is achieved, and may be used in conjunction with forms of tumor therapy such as surgery or chemotherapy with different agents. In some embodiments, the dose administered of a composition is between approximately 120 and 250 mg/m$^2$ with respect the mammalian subject to which it is administered.

The invention is further illustrated by the following examples, which are not to be construed in any way as imposing limitations upon the scope thereof. In the contrary, it is to be clearly understood that resort may be had to various other embodiments, modifications, and equivalents thereof which, after reading the description herein, may suggest themselves to those skilled in the art without departing from the spirit of the present invention and/or scope of the appended claims.

EXAMPLE 1

General Methods

A. Materials

Preliposomal Annamycin lyophilizate was prepared as a powder comprising DMPC, DMPG, and Polysorbate 20, and Annamycin.

Dimyristoyl phosphatidylcholine (DMPC) and 1,2-dimyristoyl-sn-glycero-3-[phosphor-rac-(1 glycerol)]sodium salt (DMPG) were obtained as a dry powder from Nippon Fine Chemicals, Inc., Osaka, Japan.

Annamycin, as a THF solvate (>95% pure) (MW=640.39) was synthesized as previously described with slight modifications (Horton, D., Priebe, W. 4-demethoxy-3'-desamino-2'-halo-anthracyclines and pharmaceutical compositions containing same. U.S. Pat. No. 4,537,882, 1985.)

Normal saline was obtained from Abbott Laboratories, North Chicago, Ill.

In the following example, the reconstitution of pre-liposomal Annamycin was carried out according to the following method:

Step 1: Preparation of Saline Syringes and IV Bag

All procedures were carried out in a laminar flow hood or clean room utilizing sterile technique.

Syringes (45 mL) of saline (0.9% sodium chloride, injection USP) were prepared, one for each 45 mg vial of liposomal Annamycin to be used. These syringes of saline were used for reconstitution of the preliposomal Annamycin. For example, for a 360 mg of total dose of liposomal Annamycin, eight syringes were prepared.

The syringes were placed in a 37° C. oven or IV bag warmer for at least 2-3 hours.

A non-PVC IV bag was prepared containing an additional volume of saline, equal to the total volume of saline in the syringes used for reconstitution of preliposomal Annamycin. The size of the IV bag was of sufficient volume to contain twice the volume of saline in the syringes. For example, if the total dose of study drug was 360 mg, eight (8) 45-mg vials of preliposomal Annamycin were required, each requiring 45 mL of saline or 360 mL total saline. Thus, a non-PVC IV bag was prepared which also contains 360 mL saline. This was accomplished by removal of 640 mL of saline from a standard 1,000 mL non-PVC IV bag of saline. A 1000 mL IV bag was of sufficient size to hold twice the volume of the saline remaining in the bag, i.e., 2×360 mL=720 mL.

The prepared saline IV bag was warmed, in a commercially available IV bag warmer which had been preheated per manufacturer instructions to approximately 37° C. or an oven heated to 37° C. The IV bag was placed in the bag warmer or oven prior to use in the subsequent steps for approximately 2-3 h, so that the IV bag reached a temperature of about 37° C.

Step 2: Reconstitution of Preliposomal Annamycin Lyophilizate

Vials of preliposomal Annamycin lyophilizate (45 mg of Annamycin, not including THF solvate weight, each), with a combined weight sufficient to provide the total required dose of drug, were removed from the freezer and allowed to stand at room temperature from about 30 minutes to about 2 hours. The vials were vigorously shaken to break up any dry cake of preliposomal lyophilizate Annamycin that may have formed.

The vials were moved to a laminar flow hood, and air was injected into each by means of air-filled syringe until the air pressure was equalized. Syringes of 45 mL saline were removed one at a time and utilized immediately for reconstitution from the 37° C. oven or IV bag warmer preheated to 37° C. The bag warmer or oven was positioned in the hood or next to the hood where the lyophilized preliposomal Annamycin was reconstituted in order to minimize possible cooling. The saline used for reconstitution was at 37° C. (±4 C) when mixed with the lyophilized drug product in the vials.

The syringes were removed from the bag warmer or oven one at a time, immediately prior to mixing with the preliposomal Annamycin lyophilizate. For example, a syringe of 45 mL saline was removed from the 37° C. IV bag warmer or oven, and 45 mL of 37° C. saline was added to the first 45-mg vial of preliposomal Annamycin lyophilizate, providing a final Annamycin concentration of approximately 1 mg/mL) Following addition normal pressure was achieved by use of a needle just piercing the septum. The needle was removed and the vial was immediately shaken vigorously by hand for two minutes, placed in a zip-locked plastic bag and placed back into the oven or bag warmer at 37° C.

In a similar manner, additional syringes of 45 mL saline was then removed, one at a time, from the 37° C. IV bag warmer or oven, and 45 mL of 37° C. saline was added to a each additional 45-mg vial of preliposomal Annamycin lyophilizate, shaken and placed in the sealed plastic bag. Each vial was placed in its own plastic bag and placed in the oven or bag warmer until all vials required for the total dose of preliposomal Annamycin were reconstituted.

When all vials have been reconstituted and placed in the oven or bag warmer, two to four vials were removed and shaken for an additional 1-2 minutes and then placed back in the oven or bag warmer. This was done until all vials were shaken a second time. The vials were allowed to stand for 30 min to one hour at 37° C. degrees before commencing dilution into the final IV bag as described in Step 2 below.

Particle Size Analysis of samples of the reconstituted Annamycin were carried out and determined to consistently have a mean particle size of about 8 µm, 50% distributed in the range of from about 5-10 µm and 90% distributed in the range of about 2-20 µm.

Step 3: Dilution of Liposomal Annamycin into the IV Bag

Dilution of the liposomal Annamycin was completed within approximately one hour of being reconstituted. Vials of reconstituted liposomal Annamycin, prepared as described in Step 2, were maintained at about 37° C. prior to transfer to the IV bag for dilution, and were not to be taken out of the 37° C. oven until immediately prior to the dilution.

A vial (45 mg in 45 mL saline, one at a time) of reconstituted liposomal Annamycin, prepared as described above in Step 2, containing the measured amount of saline at about 37° C. for dilution. was removed from the 37° C. oven. The vial was gently inverted, and the liposomal suspension was withdrawn via syringe. If necessary to equalize the pressure, the septum was pierced for 1 second, the needle was removed, and the withdrawal of the drug was continued. The suspension was immediately transferred slowly (so as to not generate foam) into the pre-warmed non-PVC IV bag prepared as in Step 1. Care was taken to avoid transferring any foam.

In similar fashion, the additional vials, sufficient to provide the required total dose of preliposomal Annamycin, were removed from the oven, one at a time, gently inverted, the liposomal Annamycin suspension was withdrawn via syringe and immediately transferred slowly to the contents of the pre-warmed non-PVC IV bag until all vials were transferred to the non-PVC IV bag containing saline for dilution. The saline and liposomal Annamycin in the IV bag were mixed by gently inverting the container several times, avoiding the generation of foam. The time was recorded on the IV bag. The final liposomal Annamycin concentration was approximately 0.5 mg/mL.

Throughout this step, the reconstituted liposomal Annamycin diluted IV bag was maintained at about 37° C. by immediately transferring the IV bag to the prewarmed IV bag warmer.

The IV bag warmer, when ready to be transferred to the patient infusion room was unplugged, transferred in 30 minutes-60 min and plugged in immediately near the patient for infusion. The diluted liposomal Annamycin suspension was maintained at about 37° C. leading up to and during the patient infusion.

The reconstituted liposomal Annamycin diluted with saline was stable for 24 hours when held at about 37° C. after which drug was not acceptable for administration to subjects. Only non-PVC and non-DEHP tubing were used for drug administration.

Care was taken to keep track of the time from the start of reconstitution until the completion of the 2 hour infusion. No more than 24 hours was allowed to lapse from the time of reconstitution to the time of completing the infusion.

EXAMPLE 2

Temperature Studies

An appearance test was performed on each sample. Additional appearance observations were made immediately after reconstitution of sample material at each temperature. Any changes in appearance that occurred over the duration of the particle size testing were also noted.

The appearance results obtained prior to and immediately after reconstitution of the sample material are shown below along with appearance after particle size testing. The appearances prior to reconstitution results for all samples were identical to the target limit. However, the appearance following reconstitution was dependent on temperature. As the sample temperature increases, the likelihood of undispersed particles decreases. Clusters of undispersed particles were seen at temperatures between 20-25° C., while temperatures between 28-42° C. showed no evidence of these clusters. Additionally the table shows changes in appearance following reconstitution at the end of particle size testing were limited to those at lower temperatures. These lower temperature samples had a tendency to disperse the particle clusters that were present immediately after reconstitution, though not always entirely. Unsurprisingly, the higher temperature sample's appearance remained the same because there were no undispersed clusters of particles present immediately after reconstitution.

| Temperature Variation | Appearance Prior to Reconstitution | Appearance Following Reconstitution | Additional Observations* |
|---|---|---|---|
| Nominal (37° C.) | Orange powder, free from visible contamination | Orange milky suspension; free from visible contamination of foreign material | No significant change |
| 20° C. | Orange powder, free from visible contamination | Orange milky suspension; free from visible contamination of foreign material, clusters of undispersed, un-suspended sample particles present | Fewer cluster present |
| 23° C. | Orange powder, free from visible contamination | Orange milky suspension; free from visible contamination of foreign material, one cluster of undispersed, un-suspended sample particles present | No significant change |
| 25° C. | Orange powder, free from visible contamination | Orange milky suspension; free from visible contamination of foreign material, one cluster of undispersed, un-suspended sample particles present | No clusters present |
| 28° C. | Orange powder, free from visible contamination | Orange milky suspension; free from visible contamination of foreign mate | No significant change |

-continued

| Temperature Variation | Appearance Prior to Reconstitution | Appearance Following Reconstitution | Additional Observations* |
|---|---|---|---|
| 30° C. | Orange powder, free from visible contamination | Orange milky suspension; free from visible contamination of foreign material | No significant change |
| 42° C. | Orange powder, free from visible contamination | Orange milky suspension; free from visible contamination of foreign mater | No significant change |

*These observations were made at the time of sample analysis, between approximately 1-2 hours after appearance following reconstitution The particle size study was performed using a laser diffraction particle size analyzer. A single sample was prepared and analyzed for each of the temperatures 37 (Nominal), 20, 23, 25, 28, 30, and 42° C. Each step of the sample preparation (i.e. incubation temperature, etc. . . . ) and analysis (i.e. instrument dispersant temperature, etc. . . . ) was performed at the specified temperature.

Figure 2:
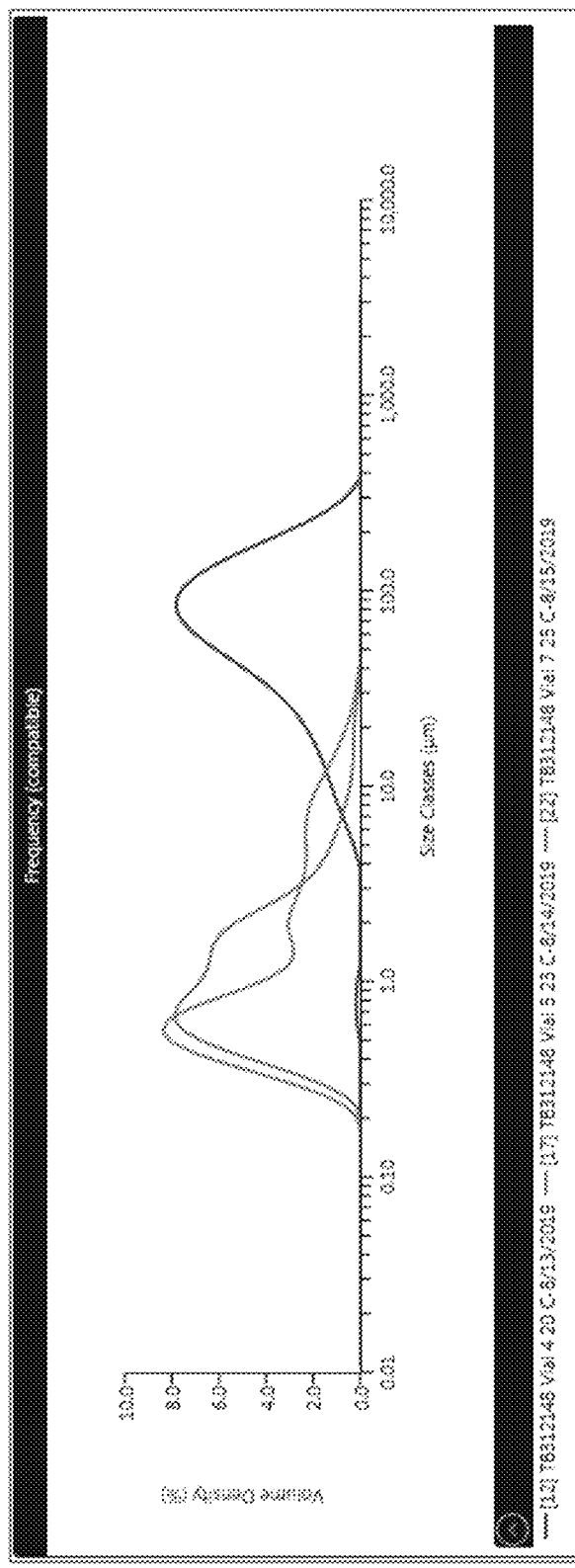
FIG. 2. A histogram result overlay for 20-25° C. samples.
Figure 3:
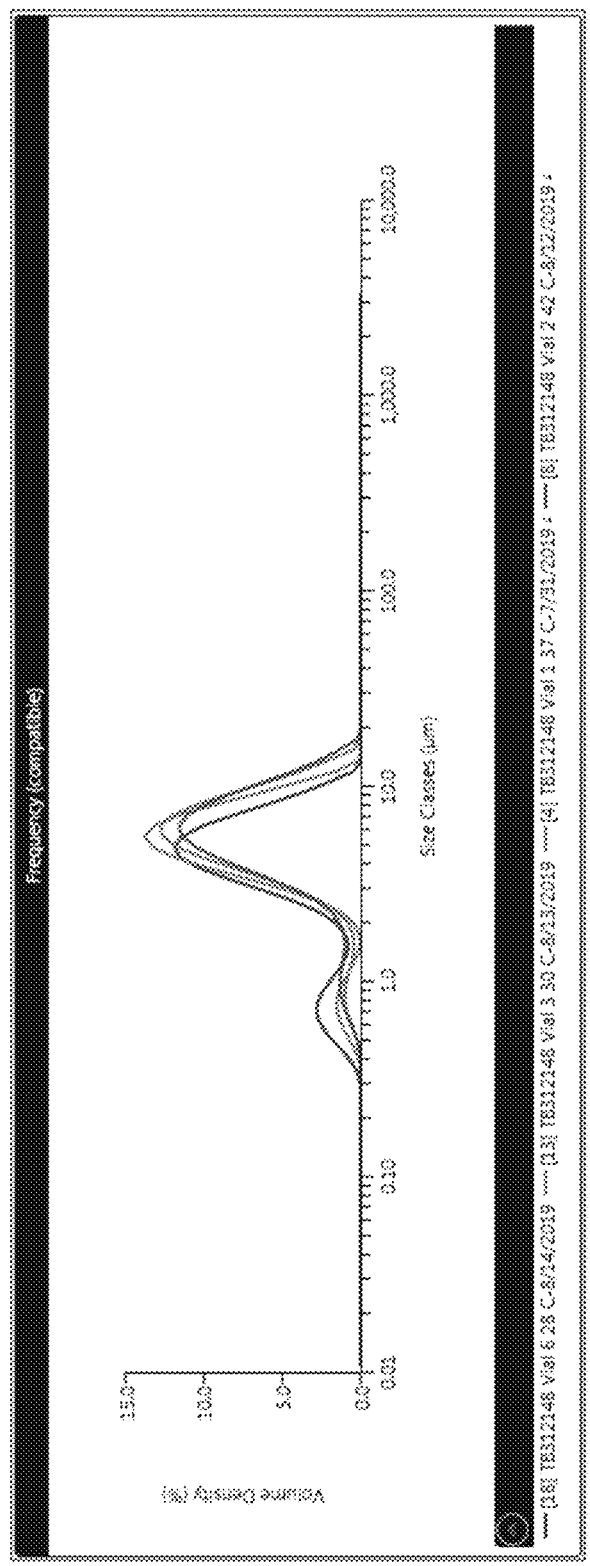
FIG. 3. A histogram result overlay for 28-42° C. samples.
Figure 4:
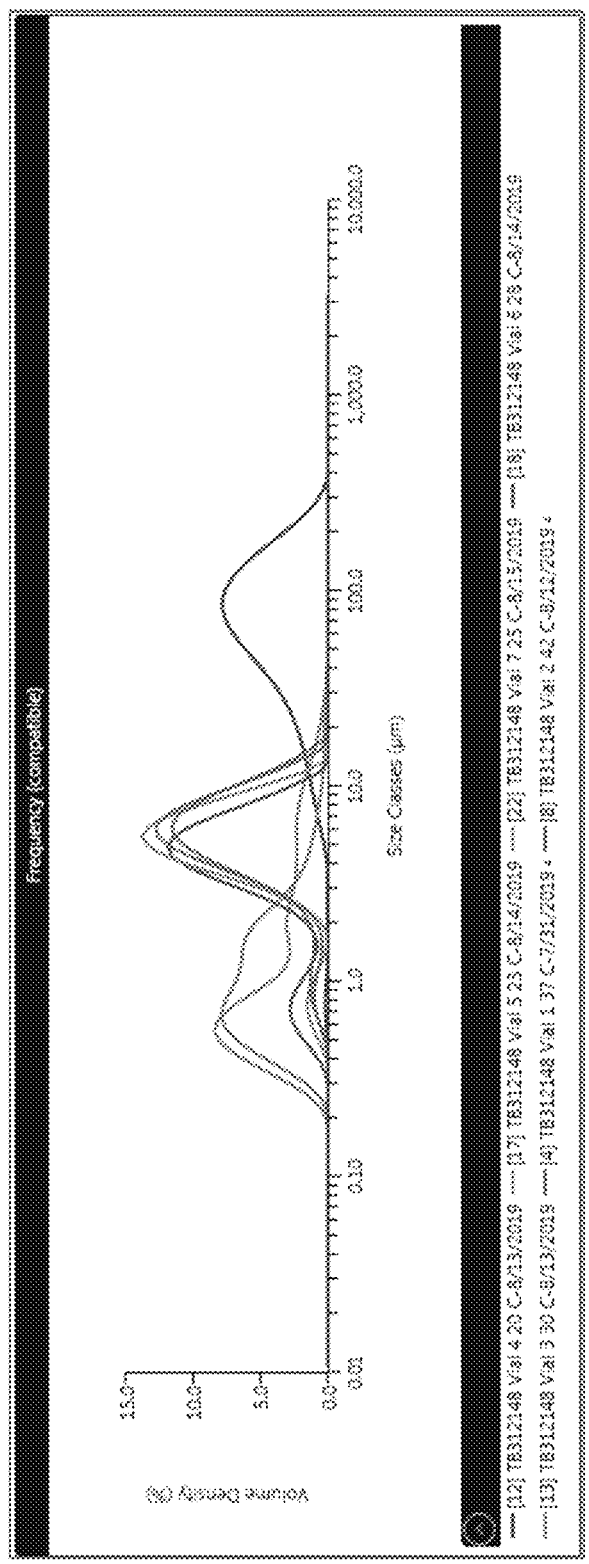
FIG. 4. A histogram result overlay for 20-42° C. samples.

The results obtained from the particle size analysis temperature study are shown below. Histogram result overlays are shown in FIGS. 2-4. Overall, particle size results for samples between 20-25° C. were significantly different than the target limits, while results for samples between 28-42° C. were similar. The extremely large particle size results for the 20° C. sample suggests the sample material did not form liposomes upon reconstitution. Results for samples between 23-25° C. were significantly smaller than the target limits, signifying the liposomes are in the processes of being formed. Results for samples between 28-42° C. are much more stable, and are similar to target limits. This indicates the liposomes have fully formed and are fairly stable in this temperature range. However, it should be noted that the 28° C. sample results do not fall within the target limits. This highlights that while there is a particle size transition that occurs in the temperature range of 25-28° C., the liposomes may not have entirely formed until a temperature of approximately 30° C. has been reached. Finally, it should be noted that when viewing the results for the 28-42° C. samples, the Dv90 result increases as temperature increases.

| Vial | Target Temp. (° C.) | Actual Analysis Temp. (° C.) | Dv10 (µm) Rounded | Dv10 (µm) Full Precision | Dv50 (µm) Rounded | Dv50 (µm) Full Precision | Dv90 (µm) Rounded | Dv90 (µm) Full Precision |
|---|---|---|---|---|---|---|---|---|
| 1 | 37* | 37.2 | 3 | 2.77 | 6 | 5.66 | 10 | 9.90 |
| 4 | 20 | 20.3 | 17 | 17.2 | 69 | 68.9 | 165 | 165 |
| | % Difference | | 467 | 521 | 1050 | 1117 | 1550 | 1567 |
| 5 | 23 | 22.8 | 0 | 0.383 | 1 | 0.872 | 8 | 7.67 |
| | % Difference | | 100 | 86 | 83 | 85 | 20 | 23 |
| 7 | 25 | 25.2 | 0 | 0.435 | 1 | 1.01 | 3 | 3.33 |
| | % Difference | | 100 | 84 | 83 | 82 | 70 | 66 |
| 6 | 28 | 28.0 | 1 | 0.796 | 4 | 4.27 | 8 | 7.63 |
| | % Difference | | 67 | 71 | 33 | 25 | 20 | 23 |
| 3 | 30 | 29.6 | 3 | 2.53 | 5 | 5.19 | 9 | 8.66 |
| | % Difference | | 0 | 9 | 17 | 8 | 10 | 13 |
| 2 | 42 | 41.9 | 2 | 2.15 | 6 | 5.60 | 10 | 10.4 |
| | % Difference | | 33 | 22 | 0 | 1 | 0 | 5 |

*Nominal
Note:
Full precision values are shown to 3 significant figures for improved data interpretation The appearance and particle size results both show temperature has an impact on reconstituted drug product liposomes particle size distribution. Reconstitution at temperatures between 20-25° C. leaves clusters of particles undispersed, while the particle size results for these temperatures vary greatly. Appearance and particle size results for temperatures between 28-42° C. are much more stable, indicating a transitional temperature range of approximately 25-28° C. All of this data indicates the drug product should be reconstituted and maintained at a temperature between approximately 30-42° C.

While the invention has been described with reference to particular embodiments and examples, those skilled in the art recognize that various modifications may be made to the invention without departing from the spirit and scope thereof.

All references cited herein, including patents, patent applications, and publications, are incorporated herein by reference, in their entirety. Whether previously specifically incorporated or not.

The various features and embodiments of the present invention, referred to in individual section above apply, as appropriate, to other sections, mutatis mutandis. Consequently, features specified in one section may be combined with features specified in other sections, as appropriate.

The foregoing description of some specific embodiments provides sufficient information that others can, by applying current knowledge, readily modify or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. In the drawings and the description, there have been disclosed exemplary embodiments and, although specific terms may have been employed, they are unless otherwise stated used in a generic and descriptive sense only and not for the purposes of limitation of the scope of the claims. Moreover, one skilled in the art will appreciate that certain steps of the methods discussed herein may be sequenced in alternative order or steps may be combined. Therefore, it is intended that the appended claims not be limited to the particular embodiment disclosed herein. Those skilled in the art will recognize, or be able to ascertain using no more than routine experimentation, many equivalents to the embodiments of the invention described herein. Such equivalents are encompassed by the following claims.

What is claimed is:

1. A method of reconstituting Annamycin, such method comprising:
    adding saline at 37° C. ±4° C. to one or more containers of preliposomal Annamycin lyophilizate, to form suspended liposomal Annamycin with a concentration of 0.5-1.5 mg/mL;
    maintaining said one or more containers at 37° C. ±4° C.;
    diluting said suspended liposomal Annamycin, with saline at 37° C. ±4° C. to provide diluted liposomal Annamycin at a concentration in saline of 0.3-0.7 mg/mL; and
    maintaining said one or more containers of suspended liposomal Annamycin and said diluted liposomal Annamycin at 37° C. ±4° C. during and after the dilution.

2. The method of claim 1 wherein said suspended liposomal Annamycin has a concentration of approximately 1 mg/mL.

3. The method of claim 1 wherein the total weight of the diluted liposomal Annamycin is equal to the effective dose required.

4. The method of claim 1 wherein the diluted liposomal Annamycin has a concentration of approximately 0.5 mg/mL.

5. The method of claim 1 wherein the
    suspension of liposomal Annamycin is maintained at 37° C. ±1° C. and the diluted liposomal Annamycin is maintained at 37° C. ±1° C.

6. A method of preparing an effective dose of a reconstituted liposomal formulation of Annamycin, such method comprising:
    warming syringes and non-PVC IV bags, each containing saline about 0.9% aqueous injection USP sodium chloride at 37° C. ±4° C. for at least about three hours, in an oven or bag warmer, wherein
        the volume of saline in mL in a syringe is equal to the weight in mg of preliposomal lyophilizate Annamycin to be reconstituted, and
        the volume of saline within said IV bag equivalent to the total amount of saline in all syringes, and
        the volume of said IV bag is of sufficient capacity to contain the total volume of saline and liposomal Annamycin for dilution of the total dose of liposomal Annamycin;
    removing a sufficient number of vials containing preliposomal Annamycin lyophilizate to provide the desired total dose of Annamycin from a freezer and allowing the vials to stand at room temperature for 30 minutes to 2 hours;
    vigorously shaking each vial of preliposomal lyophilizate Annamycin to break up any dry cake;
    injecting air into each vial from air filled syringes until pressure in each vial is equalized;
    adding a volume of 37° C. ±4° C. saline from a syringe kept at 37° C. ±4° C. in an oven to a vial containing a weight equivalent vial of preliposomal lyophilizate Annamycin such that the final Annamycin concentration is approximately 1 mg/mL, maintaining negative pressure throughout the addition of saline;
    immediately shaking the vial back and forth vigorously by hand for 15 seconds, then placing the vial in a resealable polyethylene storage bag;
    repeating the steps of adding saline, shaking the vial, and placing the vial in the storage bag until all vials required for the total dose of Annamycin are similarly prepared;
    shaking, for a second time, all vials, 2-4 at a time for 1-2 minutes;
    storing all vials of reconstituted liposomal Annamycin at 37° C. ±4° C. until ready for dilution, for 30 minutes up to 1 hour;
    removing vials of reconstituted liposomal Annamycin from storage at 37° C. ±4° C. no more than two at a time, and after gently inverting each vial once, withdrawing a foam-free suspension from the vial while maintaining negative pressure throughout the withdrawal of the suspension;
    introducing the withdrawn foam-free suspension of reconstituted liposomal Annamycin slowly into a pre-warmed non-PVC IV bag of saline at 37° C. ±4° C., prepared as described above and repeating the steps for the second vial;
    repeating the steps of removing the vials, withdrawing the suspension, and introducing the suspension into the pre-warmed IV bag until all vials of reconstituted liposomal Annamycin required for the total dose of Annamycin have been introduced into the non-PVC IV bag, providing an IV bag containing the final reconstituted liposomal Annamycin with a concentration of about 0.5 mg/mL; and
    agitating the saline and reconstituted liposomal Annamycin in the IV bag by gently inverting the container several times, without generating foam.

7. A method of treating cancer comprising administering to a patient in need thereof an effective dose of diluted liposomal Annamycin, said diluted liposomal Annamycin prepared by a method comprising:

adding saline at 37° C. ±4° C. to one or more containers of preliposomal Annamycin lyophilizate, to form suspended liposomal Annamycin with a concentration of 0.5-1.5 mg/mL;

maintaining said one or more containers at 37° C. ±4° C.;

diluting said suspended liposomal Annamycin, with saline at 37° C. ±4° C. to provide diluted liposomal Annamycin at a concentration in saline of 0.3-0.7 mg/mL;

and maintaining said one or more containers of suspended liposomal Annamycin and said diluted liposomal Annamycin at 37° C. ±4° C. during and after the dilution.

8. The method of claim 7 wherein the suspension of liposomal Annamycin is maintained at 37° C. ±1° C. and the diluted liposomal Annamycin is maintained at 37° C. ±1° C.

9. The method of claim 7 wherein said patient is human and said cancer is selected from leukemias and lymphomas.

10. The method of claim 9, wherein said cancer is selected from the group consisting of acute myeloid leukemia (AML), chronic myeloid leukemia (CML), acute lymphocytic leukemia (ALL), chronic lymphocytic leukemia (CLL), Hodgkin lymphoma, and non-Hodgkin lymphoma.

11. The method of claim 1, wherein said diluted liposomal Annamycin is maintained at 37° C. ±4° C. before and during patient infusion.

12. The method of claim 11, wherein a sleeve is used on an IV drip line to maintain said diluted liposomal Annamycin at a temperature of 37° C. ±4° C. before and during patient infusion.

13. The method of claim 6, wherein said diluted liposomal Annamycin is maintained at 37° C. ±4° C. before and during patient infusion.

14. The method of claim 13, wherein a sleeve is used on an IV drip line to maintain said diluted liposomal Annamycin at a temperature of 37° C. ±4° C. before and during patient infusion.

15. The method of claim 7, wherein said diluted liposomal Annamycin is maintained at 37° C. ±4° C. before and during patient infusion.

16. The method of claim 15, wherein a sleeve is used on an IV drip line to maintain said diluted liposomal Annamycin at a temperature of 37° C. ±4° C. before and during patient infusion.

* * * * *